Figure 1:
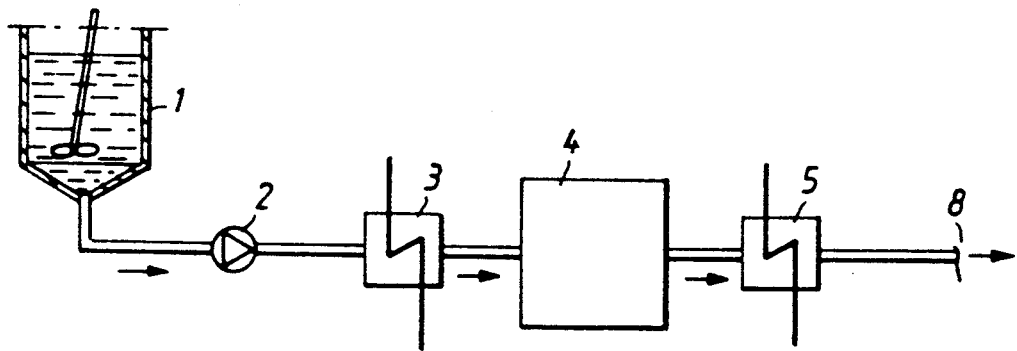

United States Patent [19]

Lundin et al.

[11] Patent Number: 5,270,271
[45] Date of Patent: Dec. 14, 1993

[54] INITIATOR SUSPENSIONS, THEIR PREPARATION AND USE

[75] Inventors: Claes Lundin, Saltsjö-Boo; Berit Simonsson, Vällingby, both of Sweden

[73] Assignee: Berol Nobel AB, Stenungsund, Sweden

[21] Appl. No.: 885,976

[22] Filed: May 20, 1992

[30] Foreign Application Priority Data

May 31, 1991 [SE] Sweden ............... 9101674

[51] Int. Cl.$^5$ ............................... B01J 35/08
[52] U.S. Cl. ...................... 502/8; 502/100; 502/160; 568/558
[58] Field of Search ............ 502/8, 151, 160, 100; 568/558, 559

[56] References Cited

U.S. PATENT DOCUMENTS 4,818,425  4/1989  Meijer ........................... 252/94

FOREIGN PATENT DOCUMENTS

| 106627 | 4/1984 | European Pat. Off. . |
| 271462 | 6/1988 | European Pat. Off. . |
| 2595097 | 4/1987 | France . |
| 2068009 | 8/1981 | United Kingdom . |

OTHER PUBLICATIONS

Research Disclosure No. 193, May 1980 No. 19302.

*Primary Examiner*—Joseph L. Schofer
*Assistant Examiner*—David Wu
*Attorney, Agent, or Firm*—Fred Philpitt

[57] ABSTRACT

A process for the preparation of an aqueous suspension of a solid free-radical forming initiator, a plant for the preparation, an initiator suspension and use of the suspension in polymerization of ethylenically unsaturated monomers. The process for the preparation of the suspension comprises the steps of:
 (a) heating the initiator to its melting point;
 (b) finely dividing the initiator in water while it is in a molten state;
 (c) rapid cooling so that the initiator is in a molten state for a period of time which is less than about 5 minutes.

The initiator suspension has very small particles and a narrow particle size distribution whereby at least 50% by weight of the particles are smaller than 5 μm and at least 90% by weight of the particles are smaller than 10 μm.

9 Claims, 1 Drawing Sheet

INITIATOR SUSPENSIONS, THEIR PREPARATION AND USE

The present invention relates to a suspension of a solid free-radical forming initiator in water, to a process and to a plant for the production of such suspension and to the use of such suspension in polymerization.

Polymerization of ethylenically unsaturated monomers, such as vinyl chloride, is often carried out in aqueous suspensions and is initiated by thermal decomposition of monomer soluble, free-radical forming compounds, for example organic peroxides or azo compounds. It is often advantageous to charge the initiator in the form of an aqueous suspension comprising small particles of solid initiator.

Peroxide suspensions for the production of PVC is for example disclosed in "PVC-Herstellung unter Anwendung von Peroxid-Suspensionen", W.F. Verhelst et al, Kunststoffe 70 (1980) 4, pages 224–228. Peroxide suspensions, their preparation and composition, are also disclosed in several patents. GB patent 2068009 describes an aqueous suspension of a solid free-radical forming initiator which suspension comprises different nonionic emulsifiers. EP patent 106627 describes a process for the preparation of an aqueous suspension of a solid organic peroxide which process comprises mixing of the peroxide, a protective colloid, a surface active agent and water at a temperature above the melting point of the peroxide.

The main requirements for initiator suspensions are that they should be easy to handle and sufficiently storage stable and further that they should not have a negative influence on the polymerization processes or on the produced polymerizates. It is further important that the actual process for the preparation of the suspension does not have a detrimental influence on the content of active initiator.

It has now been found possible to obtain initiator suspensions with a smaller particle size and a more narrow particle size distribution, with maintained high amount of remaining active initiator, than what has been possible to obtain earlier. The present initiator suspensions have excellent stability and the small particle size and narrow particle size distribution of the initiator in the suspension also give a rapid and uniform distribution of the initiator in the monomer drops at polymerization. As a result of this the resin particles in the produced polymerizate are of very equal size and the polymerizate shows a very low number of fish eyes.

The present invention relates to an improved method for the manufacture of an aqueous suspension of a solid free-radical forming initiator as defined in the claims. The method comprises the steps.

(a) heating the initiator to its melting point;
(b) finely dividing the initiator in water while it is in a molten state, preferably in the presence of one or several emulsifiers and one or several protective colloids;
(c) rapid cooling so that the initiator is in a molten state for a period of time of not longer than 5 minutes.

The initiator should preferably not be in a molten state for longer than 3 minutes. It is particularly preferred that it is in a molten state for not more than 1 minute and particularly for not more than 30 seconds. It is also preferred that the initiator is cooled to a temperature which is lower than about 20 degrees, and particularly lower than about 30 degrees, below its melting point in degrees C.

The short time in a molten state gives the result that the droplets obtained when finely dividing the initiator in water do not have the time to melt together before they solidify by the cooling. It is usually suitable to carry out the cooling so rapidly that the droplets solidify within 2 minutes, preferably within 1 minute after that they have been finely divided in the water. It is particularly preferred that the cooling is carried out in such a manner that they solidify within 30 seconds and especially within 20 seconds. However, these periods of time are approximate and depend, among other things, on the efficiency of the emulsifiers in the system. The initiator must be in a molten state when it is finely divided in water, but otherwise it is advantageous that it is in a molten form as short time as possible. The shortest time during which the initiator must be in a molten state thus depends on the efficiency of the equipment that is used The short time in a molten state also means that only very minor amounts of the active initiator are lost through thermal decomposition. The time at temperatures at or above the melting point is suitably adjusted so that not more than 2%, preferably not more than 1%, of the active initiator substance is decomposed during the treatment. It is especially preferred to adjust the time at or above the melting point so that not more than 0.5%, especially not more than 0.2%, of the active initiator is decomposed during the treatment. It is known that decomposition of free-radical forming initiators, particularly of peroxides, generally follows the first order kinetics, which means that the following equation is approximately valid:

$$k \cdot t = -\ln(P_t/P_0) \qquad (I)$$

wherein k is the velocity constant of the reaction, t is the time, $P_t$ is the amount of initiator at the time t and $P_0$ is the original amount of the initiator. The time t when a certain part x of the initiator remains at a certain temperature can thus be given as:

$$t = t_h \cdot \ln x / \ln 2 \qquad (II)$$

wherein $t_h$ is the half life of the initiator at the temperature in question. With regard to the stability of the initiator the time at temperatures at or above the melting point should suitably not exceed the time t which can be calculated from the equation (II) where x is 0.98, preferably 0.99. It is particularly preferred that the time does not exceed the time which can be calculated when x is 0.995, especially 0.998. As an example it can be mentioned that if less than about 1% of an initiator having an half life of about 30 minutes at the melting point is to be decomposed, ie that x is about 0.99 and $t_h$ is about 30 minutes, the time at the melting point should not exceed about 30 seconds. If the initiator has a half life of about 4 hours it is sufficient, with regard to stability, that the time does not exceed about 3.5 minutes.

The solid initiator is suitably first mixed with water for formation of a coarse suspension and the mixture is then heated to the melting point of the initiator. Emulsifiers and protective colloids can be added before or after the heating It is suitable that at least part of the amount of emulsifiers and protective colloids are added before the heating. Optional heat released at decomposition of the initiator is distributed in the entire mixture, whereby uncontrolled rise in temperature and accelerated decomposition of the initiator are counteracted. The fine dividing of the initiator is suitably carried out by homogenizing the coarse suspension in a heated state so that an emulsion is formed, for example by flow in narrow passages and/or by ultrasonics. A preferred manner of homogenization of the heated coarse suspension comprises flow through one or several gaps, or valves, whereby the pressure drop suitably is from about 3000 to about 150000 kPa, preferably from about 10000 to 30000 kPa, and this pressure drop is suitably over one or several gaps in series. Suitable gap-homogenizers are commercially available, for example APV Gaulin (®) In order to obtain required speed and temperature control at the heating and cooling these operations are preferably carried out by heat exchange towards warm and cold media respectively, such as water, for example in a plate-type heat exchanger.

A particularly preferred method for the manufacture of a suspension according to the invention thus comprises the steps:

(a) mixing of initiator, emulsifier, protective colloid and water for formation of a coarse suspension;

(b) heating of the coarse suspension to the melting point of the initiator;

(c) homogenization of the heated mixture for formation of an emulsion, preferably by passing it through a gap or valve homogenizer;

(d) rapid cooling of the emulsion for formation of a suspension of the solid initiator.

Suspensions according to the invention can be produced from solid free-radical forming initiators, for example peroxides, suitably organic peroxides, such as dialkyl- or diaralkyl peroxides, aromatic or aliphatic diacyl peroxides, peresters, perketals, ketone peroxides or peroxydicarbonates, preferably having a melting point above about 25° C., particularly above about 30° C. and especially above about 40° C. Preferred initiators in the present process and suspensions have a half life at the melting point which is higher than about 30 minutes, and especially higher than about 60 minutes. It is also preferred that the initiator is essentially stable at 0° C., but if it is not additives lowering the freezing point can be used in the suspension. Dialkyl peroxydicarbonates form a particularly suitable group of peroxides, for example dimyristyl-, dicetyl-, distearyl-, dicyclohexyl-, di-4-tert.butylcyclohexyl and didecyl- peroxydicarbonate. Among other suitable peroxides can be mentioned dilauroyl-, bis(o-methylbenzoyl)-, bis(m-methylbenzoyl)-, didecanoyl-, 1,1'-di-hydroxydicyclohexyl- and dicumyl- peroxide, 2,5-di-hydroxy-peroxy-2,5-dimethyl hexane and di-t-butylperoxy isophtalate. Dialkyl esters of monoperoxyoxalic acid form another preferred group of peroxides, and these are preferably such wherein the alkyl group on the perester part of the molecule is a tertiary alkyl group having from 4 to 8 carbon atoms, while the other alkyl group is a primary, normal alkyl group having from 18 to 28 carbon atoms, preferably from 18 to 24 carbon atoms. These peroxides are disclosed in more detail in EP patent 271462 and as examples of such dialkyl esters the following can be mentioned: octadecyl(t-butylperoxy)oxalate, octadecyl(t-pentylperoxy)oxalate, octadecyl(t-hexylperoxy)oxalate, octadecyl(t-heptylperoxy)oxalate, octadecyl(t-octylperoxy)oxalate, octadecyl(2,4,4-trimethyl-2-pentylperxy)oxalate, octadecyl(1-methyl-1-cyclohexylperoxy)oxalate and corresponding compounds wherein the alkyl group in the ester part of the molecule is an eicosyl, docosyl and tetracosyl group respectively. Particularly suitable such dialkyl esters are octadecyl(t-butylperoxy)oxalate, eicosyl(t-butylperoxy)oxalate, eicosyl(t-pentylperoxy)oxalate, docosyl(t-butylperoxy)oxalate, docosyl(t-pentylperoxy)oxalate, docosyl(t-hexylperoxy)oxalate, docosyl(t-heptylperoxy)oxalate, docosyl(t-octylperoxy)oxalate, docosyl-(2,4,4-trimethyl-2-pentylperoxy)oxalate and docosyl(1--methyl-1-cyclohexylperoxy)oxalate.

Among the mentioned initiators it is preferred to use diacyl peroxides, dialkyl peroxydicarbonates and dialkyl esters of monoperoxyoxalic acid. Especially preferred initiators are dilauroyl peroxide, dicetyl peroxydicarbonate, dimyristyl peroxydicarbonate, di-(4-t-butylcyclohexyl) peroxydicarbonate and docosyl(t-butylperoxy)oxalate. The initiator is preferably added in such an amount that the finished suspension contains from about 0.3 to about 4% by weight of active oxygen, particularly from about 0.5 to about 3% by weight of active oxygen, which in most cases means that the suspension contains from about 10 to about 60, preferably from about 20 to about 45% by weight of initiator.

An emulsifier in an amount of from about 0.1 to about 20% by weight, based on the suspension, is preferably added and particularly in an amount of from about 0.2 to about 10% by weight. Hereby nonionic surface active agents are preferably used, for example ethoxylated fatty alcohols, fatty acids, alkyl phenols or fatty acid amides, or ethoxylated or non-ethoxylated glycerol esters or sorbitan esters of fatty acids. Anionic surface active agents can also be used, for example alkyl- or alkylaryl sulphates, -sulphonates, -ethersulphates, -phosphates or -etherphosphates, or mono- or diesters of sulphosuccinates. Cationic and amphoteric surface active agents can also be used. The emulsifiers can be used singly or in mixtures, but anionic and cationic agents cannot be mixed.

Among protective colloids which can be used can be mentioned polyvinyl alcohol, polyvinylpyrrolidone, polyacrylic acid, acrylic acid copolymers with acryl amide or acrylic esters, water soluble cellulose derivatives such as hydroxyethyl- and hydroxypropyl-, methylhydroxypropyl- and ethylhydroxyethyl cellulose, methyl- and carboxymethyl cellulose, gelatin , starch etc.. The amount of protective colloid is selected with regard to emulsifiers and initiator so that a suitable viscosity is obtained, preferably of from about 20 to about 600 cp, measured with a Brookfield RVT viscosimeter, at 100 rpm and 20° C. From about 0.001% by weight, generally from about 0.05 to about 10% by weight and preferably from about 0.2 to about 5% by weight of protective colloid, based on the suspension, are added.

The invention also relates to an aqueous suspension of a free-radical forming initiator, which suspension can be prepared according to the above described process of the invention. It has been found possible to obtain a suspension wherein at least 50% by weight of the initiator particles are smaller than 5 μm and wherein, at the same time, at least 90% by weight of the initiator particles are smaller than 10 μm. At least 50% by weight of the initiator particles are preferably smaller than 3 μm, and especially smaller than 2 μm, while, at the same time, at least 90% by weight of the initiator particles preferably are smaller than 5 μm, and especially smaller than 4 μm. Essentially all initiator particles in the suspensions are smaller than 20 μm, particularly smaller than 10 μm. Particle size definitions refer to measurements by means of laser based light diffraction. It is preferred that the average amount of active initiator in each particle exceeds 90% by weight, which is possible to obtain according to the invention, and that the suspension contains from about 0.3 to about 4% by weight of active oxygen. The suspension is very stable and if the peroxide in itself has a sufficient chemical and thermal stability the suspension can, without problems, be stored for one or several months at room temperature (about 20° C.), without occurrence of separation or any other essential physical change. It is preferred that the suspension also contains emulsifier and protective colloid. For suitable and preferred initiators, emulsifiers and protective colloids and for amounts of these, reference is made to the disclosure concerning the preparation of the suspension according to the invention.

The invention also relates to a plant for the production of a suspension according to the invention, which plant comprises means for heating the initiator, means for finely dividing this in water, preferably a gap homogenizer, and means for rapid cooling of the finely divided mixture. The plant suitably also comprises means for mixing a solid initiator with water, emulsifier and protective colloid.

Figure 2:
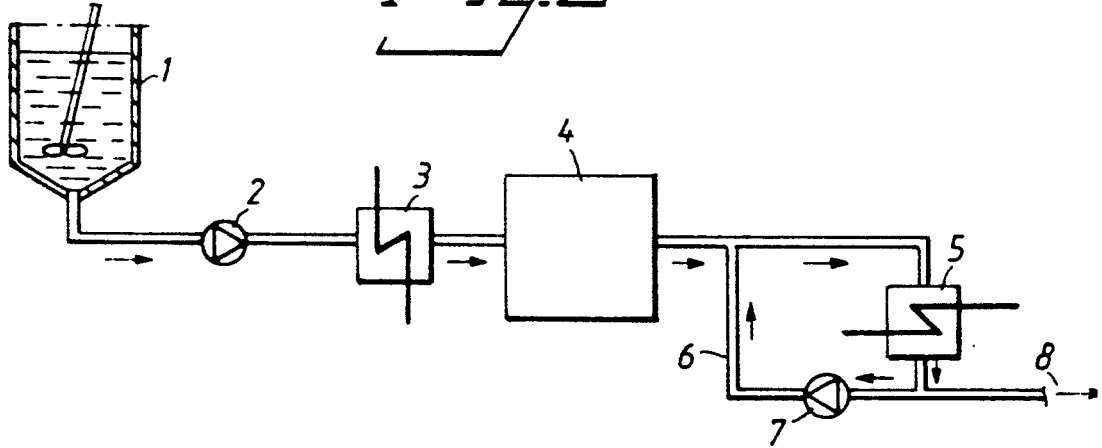
Figure 3:
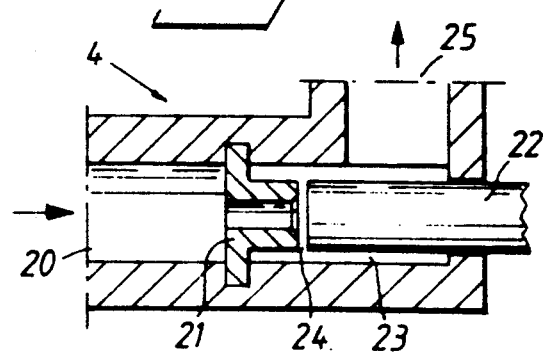

Embodiments of plants according to the invention are illustrated more in detail in the appended drawings wherein FIG. 1 and FIG. 2 schematically show two different plants for carrying out the process of the invention, while FIG. 3 schematically shows a sectional side-view of a detail of a utilizable gap homogenizer.

FIG. 1 shows a plant comprising a mixing tank 1, a pump 2, a heat exchanger 3 connected to a heating medium, for example hot water, a preferably heated gap homogenizer 4, a heat exchanger 5 connected to a cooling medium, for example cold water, and an outlet 8 for produced product, which means are connected in series. The heat exchangers 3, 5 are preferably plate-type heat exchangers, whereby very rapid heating and cooling can be achieved. The homogenizer 4 preferably comprises a high-pressure pump, for example a piston pump, and a gap, preferably an essentially ring-shaped gap, with adjustable width. At the preparation of a suspension according to the invention water, initiator, emulsifier and protective colloid are mixed to a coarse suspension in the tank 1, continuously or batch-wise. In the heat exchanger 3 the coarse suspension is heated, for example by means of hot water so that the initiator reaches a molten state. The mixture is then brought to the homogenizer 4, which it leaves in the form of an emulsion which is rapidly cooled in the heat exchanger 5, for example by means of cold water, so that a suspension of solid initiator particles is obtained. With the disclosed plant the flow and the cooling can be controlled in such a manner that the initiator is in a molten state for a suitable time, for example from about 5 or about 10 seconds up to about 30 or about 60 seconds.

FIG. 2 shows a modified plant where the outlet from the homogenizer 4 leads to a circulation system 6 with a heat exchanger 5 connected to a cooling medium and a pump 7. After the heat exchanger 5 in the circulation system there is an outlet 8 for produced product. Other parts correspond to those of the plant of FIG. 1. The production of a suspension according to the invention is carried out in the same manner as disclosed in connection with FIG. 1, with the exception that the emulsion from the homogenizer 4 is mixed with circulating cold suspension from the circulation system 6 before it reaches the heat exchanger 5 and hereby a very efficacious cooling is obtained. From about 50 to about 90% of the flow can for example be circulated through the system 6, while the remainder is taken out as product via the outlet 8.

FIG. 3 shows schematically a sectional side-view of a part of a gap homogenizer 4. A high pressure pump (not shown) leads, via a pipe 20, to a ring-shaped support which together with a head 22 forms a ring-shaped gap 24, the width of which can be adjusted by axial displacement of the head 22. The gap 24 leads to a ring-shaped space 23 which leads to an outlet 25. The homogenizer 4 can also be equipped with means for heating, for example electric heating coils, so that an essentially even temperature can be maintained all the way to the outlet 25. When the homogenizer is used heated coarse suspension flows from the high pressure pump through the pipe 20 and the gap 24. The substantial velocity increase and the turbulence which are obtained hereby give as a result that an essentially homogenous emulsion is obtained in the space 23 and the outlet 25. The axial position of the head 22 is adjusted so that a desired pressure drop over the gap 24 is obtained, for example from about 3000 to about 150000 kPa.

Finally the invention relates to a process for polymerization of ethylenically unsaturated monomers in an aqueous system, whereby a solid, monomer soluble free-radical initiator is charged to the system in the form of a suspension according to the invention. Examples of monomers which can be polymerized comprise vinyl aromatic compounds, eg styrene and substituted styrenes such as p-chloro-styrene, esters of aliphatic α-methylene carbonic acids, preferably lower alkyl esters such as methylacrylate, ethylacrylate, methyl methacrylate or ethyl methacrylate, acrylic acid nitrile, vinyl esters such as acetate, vinyl halides, vinyl ethers such as vinyl methyl ether, vinylidene chloride and lower alkenes such as butadiene. The invention is particularly useful for polymerization of vinyl chloride or vinyl chloride with up to about 20% by weight of co-polymerizable monomers, based on the vinyl chloride, such as alkenes, vinyl acetate, vinylidene chloride, acrylic or methacrylic acid, acrylates or methacrylates, acrylonitrile or methacrylonitrile, vinyl esters etc., by known suspension- or microsuspension polymerization processes. The suspension is usually added in an amount of from about 0.01 to about 2% by weight active initiator, based on the monomers.

Thanks to the fact that the initiator particles in the suspension of the invention are small and within a narrow particle size distribution range important advantages at polymerization are gained. The particle size and the narrow particle size range give a rapid and uniform distribution of the initiator in all monomer drops which thereby get a uniform initiator concentration which results in resin particles which are equal in size and in a very low number of fish-eyes in the resin and at the same time the initiator is used in a more efficacious manner. The rapid and uniform distribution also makes it possible to charge the initiator as the last component to a reaction mixture which is pre-heated to the polymerization temperature, whereby the polymerization reactor can be used more efficiently. The pre-heated reaction mixture can be prepared by elimination of all oxygen and by heating one or more components before they are charged to the reactor.

The invention is further illustrated in the following examples. Unless otherwise stated, all amounts are % by weight.

EXAMPLE 1-12

In a test plant corresponding to the one shown in FIG. 1 12 suspensions were prepared. The heat exchangers 3,5 were plate-type heat exchangers and the gap homogenizer 4 was of the mark APV Gaulin (®), model LAB100-5TBS, In each test 4 liters of a coarse suspension of dicetyl peroxydicarbonate (melting point 52° C.), emulsifier, protective colloid and water were mixed in tank 1 at 20° C. and then pumped through the heat exchanger 3, which was heated with hot water of 80°-90° C., to a temperature of about 50°-55° C. The heated mixture was then pumped through the gap homogenizer 4 which kept a temperature of about 52° C., whereby the pressure drop over the gap was about 18000 kPa. The emulsion which was hereby formed was cooled in the heat exchanger 5, with cooling water having a temperature of about 2°-4° C., to a temperature of 8°-10° C. The flow through the equipment was about 1.7 l/minute and the average dwell time between the two heat exchangers 3, 5 was about 10 seconds. The particle sizes of the suspensions were measured with a Cilas(®) granulometer 850. The viscosity of the produced suspensions was measured at 20° C. with a viscosimeter of the type Brookfield(®) RVT, spindle 3, at 100 rpm. The suspensions were stored at 20° C. for one month without any viscosity change or any sedimentation or separation.

As emulsifiers the following substances were used: Berol 08(®), which essentially is an ethoxylated stearyl alcohol (HLB=18.5), Lutensol AT80(®), which also essentially is an ethoxylated stearyl alcohol (HLB=18.5), Lutensol AT50(®), which essentially is an ethoxylated stearyl alcohol (HLB=18.0) and Atmos 150, which essentially consists of glycerol mono- and distearate (HLB=3.2). As protective colloids the following substances have been used: Ghosenol KH20(®), which essentially is a high molecular weight polyvinyl alcohol, with a degree of hydrolysis of about 78.5 −81.5 mole %, and Alcotex 72.5(®), which essentially is a low molecular weight polyvinyl alcohol with a degree of hydrolysis of about 71.5-73.5. The compositions in % by weight of the suspensions in the twelve tests are shown in the table below. The remaining content up to 100% is essentially water.

| Test. | Initiator | Emulsifier B.08 | L. AT80 | L. AT50 | A.150 | Prot. Colloid G.KH20 | A.72.5 |
|---|---|---|---|---|---|---|---|
| 1 | 30 | 0.6 | | | 0.6 | | 1 |
| 2 | 30 | 0.6 | | | 0.4 | | 1.5 |
| 3 | 30 | 0.8 | | | 0.2 | | 1.5 |
| 4 | 30 | 1.35 | | | 0.15 | | 1 |
| 5 | 30 | | 1.2 | | | | 1.5 |
| 6 | 30 | | | 1.5 | | 0.5 | |
| 7 | 35 | 0.9 | | | 0.5 | 0.2 | 0.6 |
| 8 | 25 | | 0.5 | | | | |
| 9 | 25 | 0.95 | | | 0.55 | 0.5 | |
| 10 | 25 | | | 1 | | 0.5 | |
| 11 | 25 | | | 2 | | 0.5 | |
| 12 | 25 | | | 1 | 0.5 | 0.5 | |

In the table below is shown the size in μm, whereby 50 and 90% by weight of the particles, respectively, are lower than the given size, and the viscosity in cp.

| Test. | 50 of part. smaller than (μm) | 90 of part. smaller than (μm) | visc. (cp) |
|---|---|---|---|
| 1 | 1.37 | 2.62 | 44 |
| 2 | 1.3 | 3.25 | 45 |
| 3 | 1.37 | 2.93 | 51 |
| 4 | 1.59 | 3.46 | 50 |
| 5 | 1.45 | 3.06 | 81 |
| 6 | <1.0 | 2.16 | 48 |
| 7 | 1.49 | 3.21 | 58 |
| 8 | 1.19 | 2.32 | 30 |
| 9 | 1.09 | 2.65 | 44 |
| 10 | 1.17 | 2.93 | 70 |
| 11 | 1.36 | 3.17 | 106 |
| 12 | 1.41 | 3.24 | 46 |

EXAMPLE 13

In a test plant as disclosed in Examples 1-12 a suspension of dilauroyl peroxide (melting point 56° C.) was produced. The conditions during the process were the same as used in the preparation of suspensions 1-12 except that the heating in heat exchanger 3 was carried out to a temperature of about 54°-59° C. and that the homogenizer kept a temperature of about 56° C. with a pressure drop over the gap of about 17000 kPa.

The produced suspension contained 30% by weight of the initiator, 0.8% of an ethoxylated stearylalcohol emulsifier, Berol 08(®) (HLB=18.5) and 1% by weight of a protective colloid (Alcotex 72.5(®)).

In the produced suspension 50% by weight of the particles had a size below 2.04 μm and 90% had a size below 4.22. The viscosity of the suspension at 20° C. was 120 cp. The suspension was stored at 20° C. for one month without any viscosity change or any sedimentation or separation.

EXAMPLE 14

In a test plant as disclosed in Examples 1-12 a suspension of docosyl(t-butylperoxy)oxalate (melting point 42° C.) was produced. The conditions during the process were the same as used in the preparation of suspensions 1-12 except that the heating in heat exchanger 3 was carried out with hot water having a temperature of 60°-70° C. to a temperature of about 40°-45° C. and that the homogenizer kept a temperature of about 42° C. with a pressure drop over the gap of about 21000 kPa.

The produced suspension contained 25% by weight of the initiator, 0.8% of an ethoxylated stearylalcohol emulsifier, Berol 08(®) (HLB=18.5) and 1% by weight of a protective colloid (Alcotex 72.5(®)).

In the produced suspension 50% by weight of the particles had a size below 2.28 μm and 90% had a size below 4.56. The viscosity of the suspension at 5° C. was 91 cp. The suspension was stored at 5° C. for one month without any viscosity change or any sedimentation or separation.

We claim:

1. A method for the manufacture of an aqueous suspension of a solid free-radical forming initiator which comprises the steps of
    (a) mixing a solid free radical forming initiator with water and heating the mixture to the melting point of the initiator,
    (b) finely dividing the initiator by homogenization into droplets while it is in a molten state, (c) rapid cooling so that the initiator is maintained in a molten state for a period of time not longer than 5 minutes, and (d) recovering an aqueous suspension wherein at least 50% by weight of the initiator particles are smaller than 5 μm and at least 90% by weight of the initiator particles are smaller than 10 μm.

2. A method according to claim 1 wherein the cooling is carried out so rapidly that the droplets solidify within 2 minutes after they have been finely divided in the water.

3. A method according to claim 1 wherein an emulsifier and protective colloid are added before and/or after the heating.

4. A method according to claim 1 wherein the heated coarse suspension is homogenized by flow through one or several gaps.

5. A method according to claim 4 wherein the pressure drop over the gap or gaps is from about 3000 to about 150000 kPa.

6. A method according to claim 1 when the initiator is an organic peroxide.

7. A method according to claim 1 wherein the initiator is a diacyl peroxide, a dialkyl peroxydicarbonate or a dialkylester of monoperoxyoxalic acid.

8. A method according to claim 1 wherein the initiator is dilauroyl peroxide, dicetyl peroxydicarbonate, dimyristyl peroxydicarbonate, di-(4-t-butyl-cyclohexyl) peroxydicarbonate or docosyl(t-butylperoxy)-oxalate.

9. The method of claim 1 wherein at least 50% by weight of the initiator particles in step (d) are smaller than 3 μm and at least 90% by weight of the initiator particles are smaller than 10 μm.

* * * * *